(12) United States Patent
Jia et al.

(10) Patent No.: US 11,666,242 B2
(45) Date of Patent: *Jun. 6, 2023

(54) LOCALIZATION OF OBJECTS WITHIN A CONDUCTIVE VOLUME

(71) Applicant: CARDIOINSIGHT TECHNOLOGIES, INC., Independence, OH (US)

(72) Inventors: Ping Jia, Solon, OH (US); Qingguo Zeng, Solon, OH (US); Charulatha Ramanathan, Solon, OH (US); Ryan Bokan, Cleveland, OH (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 589 days.

This patent is subject to a terminal disclaimer.

(21) Appl. No.: 16/787,828

(22) Filed: Feb. 11, 2020

(65) Prior Publication Data

US 2020/0170540 A1    Jun. 4, 2020

Related U.S. Application Data

(63) Continuation of application No. 14/867,716, filed on Sep. 28, 2015, now Pat. No. 10,568,540.

(Continued)

(51) Int. Cl.
*A61B 5/06* (2006.01)
*A61B 5/053* (2021.01)
*A61B 5/0538* (2021.01)

(52) U.S. Cl.
CPC .............. *A61B 5/063* (2013.01); *A61B 5/053* (2013.01); *A61B 5/0538* (2013.01); *A61B 2560/0223* (2013.01); *A61B 2560/0276* (2013.01)

(58) Field of Classification Search
CPC combination set(s) only.
See application file for complete search history.

(56) References Cited

U.S. PATENT DOCUMENTS

| 6,308,093 B1 | 10/2001 | Armoundas et al. |
| 2004/0254437 A1 | 12/2004 | Hauck et al. |

(Continued)

FOREIGN PATENT DOCUMENTS

| EP | 1757227 A2 | 11/2008 |
| EP | 2064987 A1 | 6/2009 |

(Continued)

OTHER PUBLICATIONS

European Patent Application No. 15844438, Applicant: CardioInsight Technologies, Inc.; Filed Sep. 28, 2015; Supplementary European Search Report, Date of Completion: Apr. 19, 2018; 10 pgs.

(Continued)

*Primary Examiner* — Yi-Shan Yang
(74) *Attorney, Agent, or Firm* — Tarolli, Sundheim, Covell & Tummino LLP

(57) ABSTRACT

An example method includes applying a localization signal to a source electrode positioned within a conductive volume and a ground electrode at a known location. Electrical activity is sensed at a plurality of sensor electrodes distributed across an outer surface of the conductive volume. The locations of each of the sensor electrodes and the location of the ground electrode being stored in memory as part of geometry data. The electrical activity sensed at each of the sensor electrodes is stored in the memory as electrical measurement data. The method also includes computing a location of the source electrode by minimizing a difference between respective pairs of source voltages determined for the plurality of sensor electrodes. The source voltage for (Continued)

each of the sensor electrodes is determined based on the electrical measurement data and the geometry data.

20 Claims, 6 Drawing Sheets

Related U.S. Application Data

(60) Provisional application No. 62/056,214, filed on Sep. 26, 2014.

(56) References Cited

U.S. PATENT DOCUMENTS

| | | |
|---|---|---|
| 2006/0084971 A1 | 4/2006 | Beatty et al. |
| 2008/0190438 A1* | 8/2008 | Harlev .................. A61B 5/0538 128/898 |
| 2009/0118620 A1 | 5/2009 | Tgavalekos et al. |
| 2011/0098594 A1 | 4/2011 | Hauck |
| 2012/0197111 A1 | 8/2012 | Bar-Tal |
| 2012/0277567 A1* | 11/2012 | Harlev .................... A61B 5/30 600/374 |
| 2014/0221803 A1 | 8/2014 | Bar-Tal et al. |
| 2014/0275991 A1 | 9/2014 | Potter et al. |

FOREIGN PATENT DOCUMENTS

| | | |
|---|---|---|
| WO | 2001025822 A1 | 4/2001 |
| WO | WO-0125822 A1 * | 4/2001 ............. A61B 5/042 |

OTHER PUBLICATIONS

International PCT Application; International Search Report and Written Opinion; PCT International Application No. PCT/US2015/052647; Filed 28 Sep. 28, 2015; Applicant: CardioInsight Technologies, Inc.; Date of Completion: Nov. 23, 2015; Authorized Officer: Jong Kyung Lee; 10 pgs.

\* cited by examiner

LOCALIZATION OF OBJECTS WITHIN A
CONDUCTIVE VOLUME

CROSS-REFERENCE TO RELATED
APPLICATIONS

This application is a continuation of U.S. patent application Ser. No. 14/867,716, filed Sep. 28, 2015, and entitled LOCALIZATION OF OBJECTS WITHIN A CONDUCTIVE VOLUME, which claims the benefit of priority to U.S. provisional patent application No. 62/056,214, filed Sep. 26, 2014, and entitled NAVIGATION OF OBJECTS WITHIN THE BODY, which is incorporated herein by reference in its entirety.

TECHNICAL FIELD

This disclosure relates to navigation of objects within a body.

BACKGROUND

This section provides background information related to the present disclosure and is not necessarily prior art.

A navigation system can locate an object within a volume. For example, a navigation system can be used to track an instrument during a procedure, such as a surgical procedure. Various systems can be used to track instruments including electromagnetic systems, optical systems, magnetic systems acoustic systems, and the like. However, existing techniques tend to be insufficiently accurate or are incapable of real-time applications.

SUMMARY

This disclosure relates to localization of objects within a conductive volume.

As one example, a system includes a plurality of sensors configured to sense electrical activity at locations distributed across an outer surface of a conductive volume, locations of each of the plurality of sensors being predetermined with respect to a spatial coordinate system and stored in memory as geometry data. A source electrode is positioned within the conductive volume at a location that is to be determined. A signal generator is to supply electrical energy to the source electrode, corresponding to a source voltage, which generates an electric field. A location calculator is configured to compute the location of the source electrode by minimizing a difference between source voltages determined for multiple pairs of the plurality of sensors. The source voltage for each pair of the plurality of sensors being determined based on sensor measurements for each respective one of the plurality of sensors in response to corresponding electric field and the geometry data.

As another example, a method includes applying a localization signal to a source electrode positioned within a conductive volume at a location that is to be determined and a ground electrode on an outer surface of the conductive volume a location of ground electrode being known. Electrical activity is sensed at a plurality of sensor electrodes distributed across the conductive volume. The locations of each of the sensor electrodes and the ground electrode being stored in memory as part of geometry data. The electrical activity sensed at each of the sensor electrodes in response to the applied localization signal is stored in memory as electrical measurement data. The method also includes computing the location of the source electrode by minimizing a difference between source voltages determined for multiple pairs of the plurality of sensor electrodes. The source voltage for each of the sensor electrodes is determined based on the electrical measurement data and the geometry data.

As yet another example, a computer-readable medium stores data and instructions executable by a processor. The data includes geometry data representing locations of each of a plurality of sensors and measurement data representing sensed electrical measurements for each of the plurality of sensors of a corresponding electric field generated in response to applying a field of a source electrode within the conductive volume. The instructions comprise a location calculator to compute a position for location of the source electrode within the conductive volume by minimizing a difference between source voltages determined for multiple pairs of the plurality of sensors, the source voltage for each of the plurality of sensors being determined based on the measurement data including sensor measurements for each respective one of the plurality of sensors in response to the corresponding electric field and the geometry data.

DETAILED DESCRIPTION

This disclosure relates to systems and methods to determine location of an object within a volume conductor. For example, the approach can be implemented by using an arrangement of sensors distributed across the volume conductor (e.g., invasively and/or non-invasively across the volume) for navigation and/or localization of an object, such as a catheter. By knowing, a priori, the spatial position for each of the sensors with respect to a coordinate system of the volume conductor, the spatial position of a source object can be ascertained with respect to the same coordinate system based on electrical signals that are emitted from the object and measured by the sensors. For example, the unknown location of the source object can be determined by minimizing a difference between source voltages determined for different pairs of the plurality of sensors. The source voltage for each pair of sensors is determined based on sensor measurements of a respective one of the plurality of sensors in response to the corresponding electric field (which is generated in response to supplying electrical energy to the source electrode) and the geometry data. As a result, an absolute spatial position of the object can be determined with a high level of accuracy, such as for localization of the object or to facilitate its navigation to a desired site within the body.

The computed location can be further employed to display graphically an indication of position for the source, such as can correspond to one or more electrodes on a catheter or other probe. A collection of location information can be collectively displayed to represent a surface or incorporated in a graphical map of patient anatomy or generic model by co-registering the determined location coordinates with anatomical geometry (e.g., for a given patient or a generic model).

Figure 1:
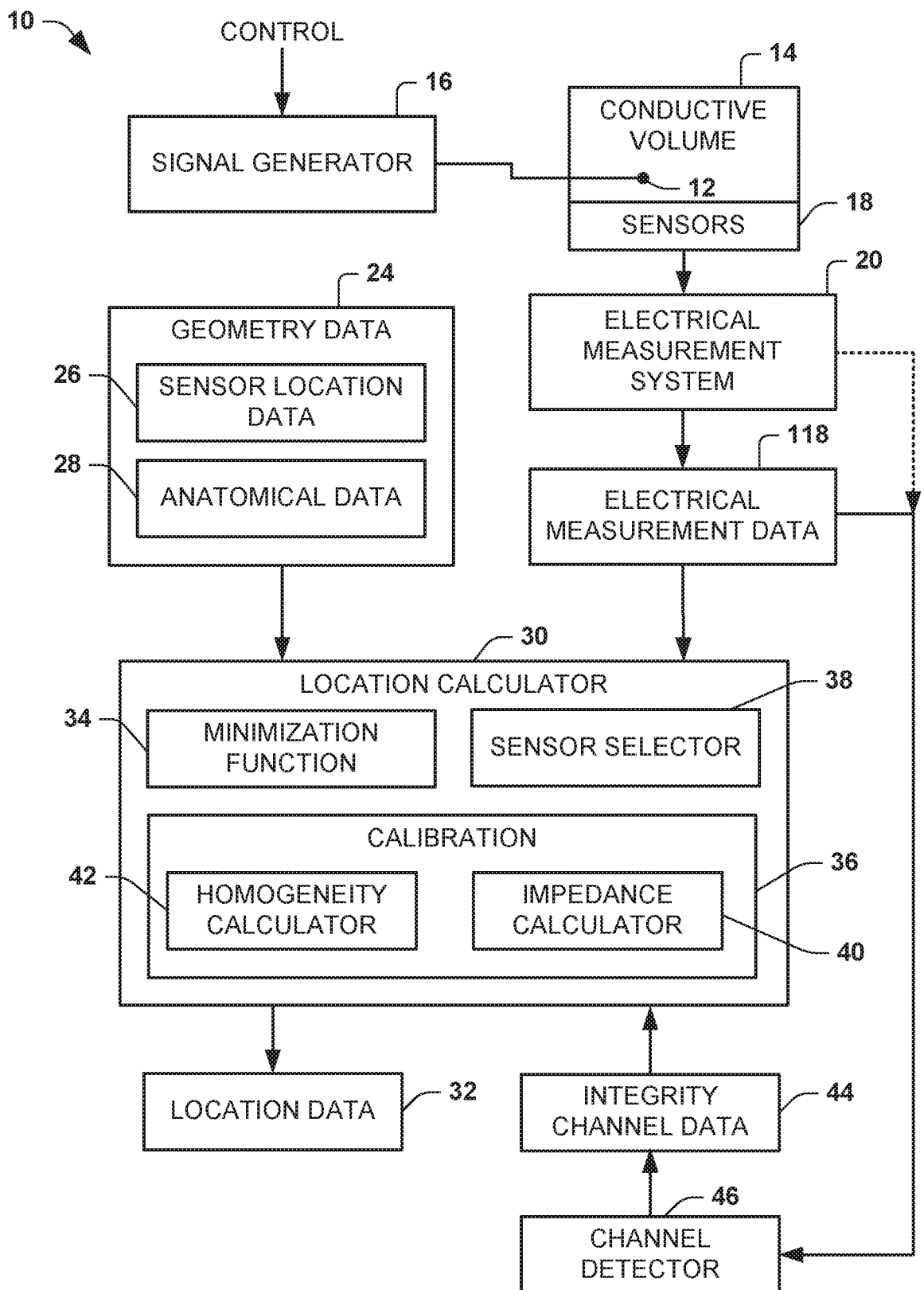
FIG. 1 depicts an example of a system to determine a location of source within a conductive volume.

FIG. 1 depicts an example of a system 10 for localizing a source 12 that is positioned within a conductive volume 14. The conductive volume can be a patient's body or some other conductive media in which the source is being localized. As disclosed herein, the source 12 can be a source electrode or multiple electrodes that can be positioned within and, in some cases, be moveable within the volume 14. For example, the source 12 is an electrode that is carried on a surface of a probe, such as a catheter or other apparatus.

A plurality of sensors 18 can be positioned across the conductive volume 14, which may include sensors on an external surface of the conductive volume 14 and/or within the volume. The locations of the sensors 18 are known in a corresponding coordinate system that describes the spatial geometry of such sensors in three-dimensional space. The locations of the sensors 18 can be determined from imaging and/or other means (e.g., digitizer, self-discovery or using one set of the sensors to detect another set of the sensors). As one example, the sensors 18 can correspond to a high-density arrangement of surface sensors that are distributed over a portion of exterior surface of the conductive volume 14 for measuring electrical activity (e.g., electrocardiograms (ECGs) of a patient's heart). An example of a non-invasive sensor array that can be used is shown and described in International application No. PCT/US2009/063803, filed 10 Nov. 2009, which is incorporated herein by reference. Other arrangements and numbers of sensors 164 can be used. Additionally or alternatively, in other examples, the sensors 18 may be sensor electrodes positioned within the conductive volume at respective locations known in the coordinate system.

A signal generator 16 can be electrically connected with the source object 12 for supplying electrical energy to the object, corresponding to a source voltage. The supplied electrical energy (e.g., current or voltage) generates the corresponding electric field in the conductive volume that can be measured by the sensors 18. An electrical circuit path can extend from the signal generator and the conductive volume 14. For example, the circuit path extends from the signal generator 16 to the source 12, from the source to a corresponding ground electrode, which is on the surface of the conductive volume at a known position, and from the ground electrode back to the signal generator.

The sensors 18 each provide sensor signals to an electric measurement system 20 representing electrical activity measured by each respective sensor. The electrical measurement system 20 is configured to receive signals from each of the sensors 18. While demonstrated as separate from the sensors 18 in the example of FIG. 1, the electrical measurement system 20 can include the sensors 18, which can include non-invasively and/or invasively positioned at known fixed locations sensors across the conductive volume (e.g., a patient's body). In some examples, one or more invasive sensors can be movable within the patient's body, such as can be attached to a probe (e.g., a catheter). The source electrode 12 that is being localized can be mounted to the same probe object and at a fixed, known relative position as such invasive sensors, such as to enable the position of the probe object and its complement of one or more sensors to also be determined by the location calculator 30.

The electric measurement system 20 thus can perform processing of the sensor signals (e.g., including filtering and/or amplification) to provide corresponding electric measurement data 22. The electric measurement data 22 can be stored in the corresponding memory. The electrical measurement data 22 thus provides signal measurements for discrete known locations based upon the sensed electrical signals by each of the sensors 18 implemented by the system. Each electrical measurement in the data 22 can include time stamps, such as from a system clock. The localization signal applied by the signal generator 16 can also be indexed to the same time base to enable synchronization of the measurement data with the signal being localized.

The system also includes geometry data 24, which is demonstrated as including sensor location data 26 and anatomical data 28. The sensor location data 26 represents location of each of the sensors 18 that has been determined with respect to a spatial coordinate system. The spatial coordinate system can be registered with structural features of the conductive volume. For example, the sensor locations 18 can be registered in a spatial coordinate system in which the patient's anatomy has also been registered, such as to enable determining coordinates of the object 12 with respect to the spatial coordinate system. The anatomical data 28 can include geometry information associated with the conductive volume 14 including the surface geometry of the outer surface thereof to which the sensors 18 have been affixed as well as boundaries of internal features within the conductive volume. The anatomical data 28, for example, represents the boundary of the heart, including one or more of epicardial or endocardial surfaces thereof.

The geometry data 24 can be generated in various ways. As one example, the geometry data can be provided based on imaging data of the conductive volume while sensors 18 are applied to its surface. An image processing system can process the acquired image data from the imaging system (e.g., corresponding to one or more imaging modality) and provide the geometry data 18. The image processing can include segmentation of anatomical features from the digital image data, which can identify structural boundaries and fiducial markers of patient anatomy and sensor locations within the image space. Examples of imaging modalities include ultrasound, computed tomography (CT), 3D Rotational angiography (3DRA), fluoroscopy, magnetic resonance imaging (MRI), X ray, positron emission tomography (PET), and the like. Such imaging can be performed separately (e.g., before or during the measurements) utilized to generate the geometric data.

As another example, the sensors can be configured to determine their location via self-discovery. For instance, a specific programmed sequence of current/voltage can be applied among electrodes, and the spatial distribution of the electrodes, with respect to each other or a neutral point, can be computed. This 'self discovery' lead set could be registered to the CT or into another three-dimensional coordinate system using a registration technique, such as disclosed herein. Additionally or alternatively, the geometrical location of the sensors can be determined via direct registration (e.g., digitization using a digitizer device or recording manual physical measurements).

The system 10 also includes a location calculator 30 configured to compute location data 32 that represents a position for the source 12 based on the electrical measurement data 22 and the geometry data 24. The location data 32 thus specifies the location of the object 12 in a corresponding spatial coordinate system, which can be registered to the conductive volume 14. For example, the location calculator 30 implements a minimization function 34 configured to minimize a difference between source voltage values determined for each of a plurality of pairs of the sensors 18.

The minimization function 34 can be programmed to compute a respective source voltage for the object 12 based upon the sensor measurements provided in electrical measurement data for each respective one of the plurality of sensors 18 in response to a corresponding electric field that is generated by the source 12 when supplied electrical energy from the signal generator 16. The minimization function 34 also utilizes sensor location data for each of the pairs of sensors as part of each source voltage calculation. The minimization function 34 is configured to compute the source location in a corresponding spatial coordinate system based on the electrical measurement data 22 from each selected pair of sensors and associated location data 26 for the selected sensors. As disclosed herein, the selection of each sensor pairs can be controlled based on the geometry data 24, the electrical measurement data 22, channel integrity and/or be in response to a user selection (e.g., via user input).

Since the plurality of the sensors 18 are distributed around the conductive volume 14 the electric measurement data 22 for a given electrical signal supplied by the signal generator 16 are temporally and spatially consistent. Thus, the location calculator 30 can compute the position based on the electrical measurement data 22 that has been acquired concurrently for each of the sensors 18 in response to the corresponding electric field that is generated in response to the signal supplied by the signal generator 16 to the source. A control signal can activate the signal generator 16 to periodically (or intermittently) supply the source signal. The electrical measurement system can store the electrical measurement data 22 with time stamps, such as from a system clock. The localization signal applied by the signal generator can also be indexed to the same base to enable synchronization of the measurement data 22 with the signal being localized. The measurement data record can also include a field specifying to which sensor the sensed measurement belongs. The sensor identifying information can also be used to access the location data 26 for each respective sensor.

The location calculator 30 includes a sensor selector 38 to select and retrieve measurement data 22 for each respective pair of the sensors 18 for use by the minimization function 34. Of the available set of sensors 18 (e.g., at least 3, such as greater than 20 sensors), for example, the sensor selector 38 selects three or more different pairs of the sensors from the plurality of available sensors 18. In some examples, the sensor selector can select each available pair of sensors for use in computing the location of the source 12. In other examples, the sensor selector 38 selects a proper subset of the available pairs of the sensors 18.

By way of example, the sensor selector 38 selects the respective sensors in response to user input (e.g., via a graphical user interface). For instance, a user can specify one or more sensors to be included or excluded from the minimization function 34. Alternatively or additionally, the sensor selector 38 can be programmed to automatically determine which pairs of sensors to utilize when executing the minimization function 34. For instance, to increase the sensitivity of detection of electrical fields, the sensor selector 38 can choose an optimal subset of electrodes based on other various characteristics, for example, lead vector, solid angle subtended by each field (sensor) point on the body surface. The respective pairs of sensors utilized in calculations performed by the minimization function 34 can be selected in response to a calibration engine 36 that is a preprogrammed method for calibrating the location calculator 30 including the minimization function 34. The calibration engine 36 can drive the sensor selector 38 based on the electrical measurement data 22 and/or geometry data 24.

As one example, the calibration engine 36 is configured to group the plurality of sensors 18 into two or more subsets of sensors. The location calculator 30 thus can apply the minimization function 34 to compute the source location by minimizing the difference between source voltages (e.g., represented by the electrical measurement data 22) that can be determined for each respective pair of sensors in each of the subsets that have been identified. If more than two subsets of sensors are identified by calibration engine 36, location calculator 30 can compute the system by aggregating the position values that have been separately computed for each of the respective subsets of sensors.

As an example, the minimization function 34 can be configured differently (e.g., employ different conductivity or resistivity values) for each subset of sensors. The different groups of sensors can reside in different regional volume or pairs of sensors that form each group can be interspersed across the surface of the volume 14. In this way, the minimization function 34 can be tailored according to the unique spatial and/or electrical characteristics in each group of the sensors.

As a further example, the calibration engine 36 can include an impedance calculator 40 configured to compute impedance for at least a portion of the conductive volume 14 based upon the electrical measurement data 22 and/or geometry data. For example, sensors 18 can further be configured to apply fields to the surface of the conductive volume which can be detected by other sensors distributed thereon. By applying fields and sensing respective fields pass the conductive volume 14 an indication of impedance throughout the volume can be ascertained. Thus, the impedance determined through corresponding portions of the conductive volume can be utilized by the sensor selector 38 to identify respective groups of the sensors 18, such as according to the relative impedance between respective pairs of sensors.

As yet another example, the calibration engine 36 includes a homogeneity calculator 42 to determine indication of homogeneity or inhomogeneity of impedance throughout the volume 14. For example the homogeneity calculator 42 can determine the indication of homogeneity (or inhomogeneity) within the conductive volume between respective pairs of the sensors 18. The indication of homogeneity can be determined as a relative index of homogeneity that can be determined for the conductive volume residing between respective pairs of the sensors 18. For example, the homogeneity calculator computes the index of homogeneity based on the impedance values computed by the impedance calculator 40 for different pairs of sensors across the volume 14. As disclosed herein, the impedance values can be based on measuring electrical characteristics between pairs of sensors (e.g., part of measurement data 118). The sensor selector 38 thus can employ relative indication of homogeneity to group the sensors into two or more subsets of sensors. The resulting pairs of sensors within each group can thus be considered to have a sufficient level of homogeneity within the conductive volume between the pairs to improve computational accuracy of the minimization function 34, such as disclosed herein.

Figure 4:
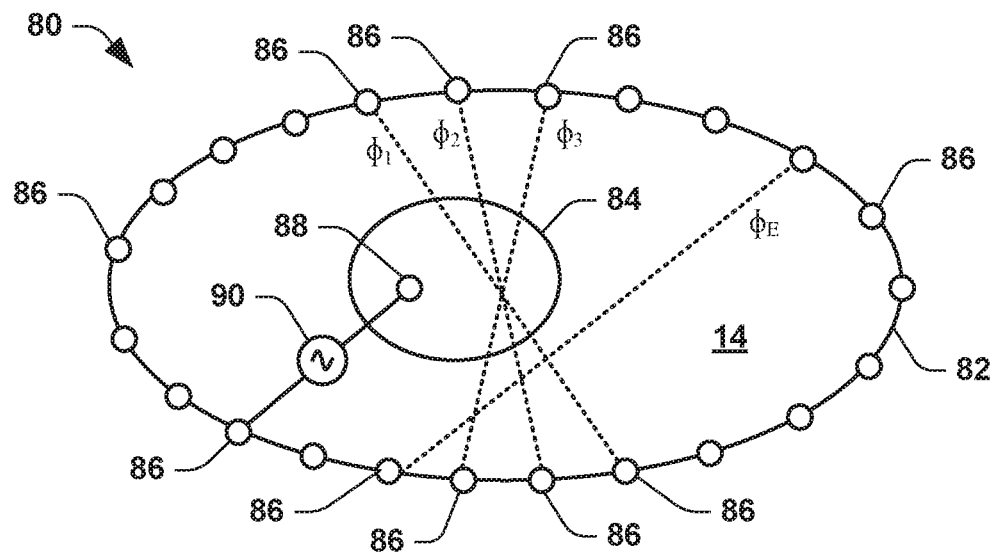
FIG. 4 depicts an example of a schematic cross-sectional view of body demonstrating relationships between one-to-one pairings of external sensors and between an internal signal source in the heart and an external sensor.
Figure 5:
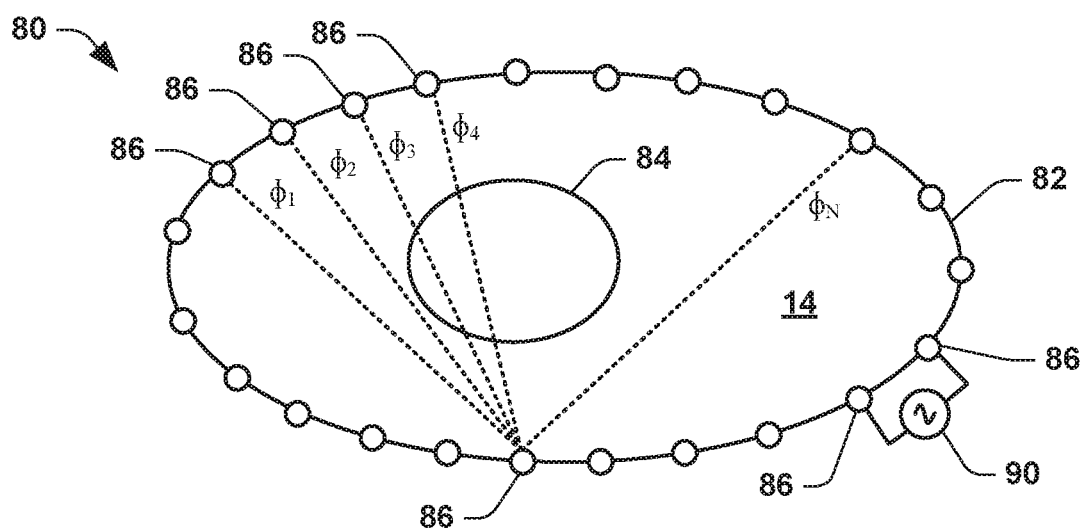
FIG. 5 depicts an example of a schematic cross-sectional view of body demonstrating relationships between a reference sensor paired with each of an arrangement of other external sensors.

By way of further example, FIGS. 4 and 5 demonstrate examples of but two approaches that can be utilized to characterize impedance and/or homogeneity of a conductive volume 14 based on electrical measurement of applied electric fields (e.g., referred to as calibration fields). The calibration fields could be bipolar (e.g. two poles of the catheter) or unipolar (between a source and a neutral reference or ground electrode). Each of the examples of FIGS. 4 and 5 demonstrate a cross-sectional view of the volume conductor, demonstrated at 80 (corresponding to volume 14 of FIG. 1), which depicts the external surface boundary of the volume (e.g., the patient's skin) 82 as well as an internal structure (e.g., the patient's heart) 84 along a virtual plane. Additionally, a plurality of electrodes 86 (corresponding to sensors 18 of FIG. 1) are disposed on the surface 82, such as evenly distributed around the volume. In the example of FIG. 4, an internal electrode 88 is also depicted within the volume conductor, such as may reside within or otherwise contact on the internal structure 84.

In some examples, the surface electrodes 86 are configured for both measuring and delivering electric fields from their noninvasive (e.g., external) location into the body. The same electrodes 86 used for sensing electrical activity from the body surface thus can be used to deliver the electric fields. In other examples, different electrodes 86 can be positioned at the same of different predetermined locations as the sensing electrodes to deliver the electric fields between respective pairs of electrodes 86, 88. Thus, a signal generator 90 can apply electrical field (e.g current or voltage) can be injected through one or more sets of electrodes 86, 88.

The electrodes 86, 88 thus can be used as sense electrodes to detect an applied electric field from various locations around or near the thorax, which can be used by the calibration engine 36 (e.g., including calculators 40 and/or 42) to help characterize the thoracic impedance and/or homogeneity of the volume. The values computed by calculators 40 and/or 42 can be determined in real-time computations and/or be stored in a look up table for compensating for impedance related errors in solving the minimization function 34.

In the example of FIG. 4, the signal generator 90 applies the electrical energy (e.g., AC signal having a prescribed frequency) between a pair of electrodes that include both a non-invasive external electrode 86 and an internal electrode 88. In the example of FIG. 5, the signal generator 90 applies the electrical energy between a pair of non-invasive external electrodes 86 to generate a corresponding electric field. The field injection (e.g. current or voltage) and sensing from different pairs/sets of electrodes can be implemented to occur in a pre-programmed time sequence, or concurrently but with different frequencies for different sets of electrodes. The injected calibration field can be a dipolar or unipolar field, and be injected between any pairs of electrodes, invasive or non-invasive. For instance, current/voltage can be injected between pairs or electrodes through time/frequency division multiplexing and the resulting fields can be sensed by other pairs of electrodes 86.)

The resulting electric field that is generated can be measured (e.g. as current or voltage) at other sensor electrodes 86 on the body surface, which sensed field can be employed by impedance calculator 40 to characterize impedance through the conductive volume 14, such as between respective electrode pairs. Additionally or alternatively, the resulting field can be measured and used by the homogeneity calculator 42 to specify homogeneity across the volume.

Additionally or alternatively, referring back to FIG. 1, the impedance inhomogeneity of the conductive media between any pair of sensors 18 can be determined from imaging data, such as CT or MRI images (e.g., represented as part of the anatomical data 28). The inhomogeneity (or homogeneity) can be determined by the calibration engine 36 so that the source voltage computations implemented by the minimization function 34 for each pair of sensors are adjusted accordingly to account for the corresponding level of inhomogeneity.

In some examples, the location calculator 30 employs channel integrity data 44 to determine if data 22 and 24 for any of the sensors 18 should be omitted from the localization methods. For example, a channel detector 46 can process the electrical measurement data 22 and/or receives feedback information from the electrical measurement system 20 to provide the channel integrity data 44 indicating which channels may provide erroneous results. The channel detector 46 can implement the functions and methods corresponding to channel integrity detection system disclosed in respect to U.S. Patent Pub. No. 2013/0304407, which is incorporated herein by reference. Other channel integrity analysis approaches could also be utilized. For example, short circuits, open circuits or other sensing issues can be utilized to identify or generate the channel integrity data 44. The sensor selector 38 thus can identify and remove bad channels (e.g., flag with metadata) and provide the remaining subset of sensors 18 as the available asset of corresponding electrical measurement data 22 and associated geometry data 24 to be utilized by the location calculator 30 in computing the location data 32.

The location data 32 thus can represent the computed location as an absolute (or relative) position in such given coordinate system at one or more time instances as a function of the electrical measurement data 22 that has been synchronized with applied localization signal (e.g., aligning data using associated time stamps). By repeating the localization over time, the movement of the source object 12 (e.g., corresponding to a probe or other movable object) may be tracked over time, such as represented by a time sequence of the location data 32. In some examples, the location data 32 for each tracked probe can be averaged over time to provide a smooth and robust display of the source's location. The averaging can also adopt other prior information such as the adjacent probe distance or the like. The location data 32 thus can be utilized to generate a visualization of the source location, such as can be provided in a graphical map that includes the patient's anatomy.

The location calculator 30 thus generates the location data 32 to represent the location of the object 12 within a given coordinate system (e.g., based on the geometry data 24). The location data 32 thus can represent the computed location as an absolute position in such given coordinate system at one or more time instances as a function of the electrical measurement data 22 that has been synchronized with applied localization signal (e.g., aligning data using associated time stamps). By repeating the localization over time, the movement of the source object 12 (e.g., corresponding to a probe or other movable object) may be tracked over time, such as represented by a time sequence of the location data 32. In some examples, the location data 32 for each tracked probe can be averaged over time to provide a smooth and robust display of the probe's location. The averaging can also adopt other prior information such as the adjacent probe distance or the like. The location data 32 thus can be utilized to generate a visualization of the location, such as can be provided in a graphical map that includes the patient's anatomy.

Figure 2:
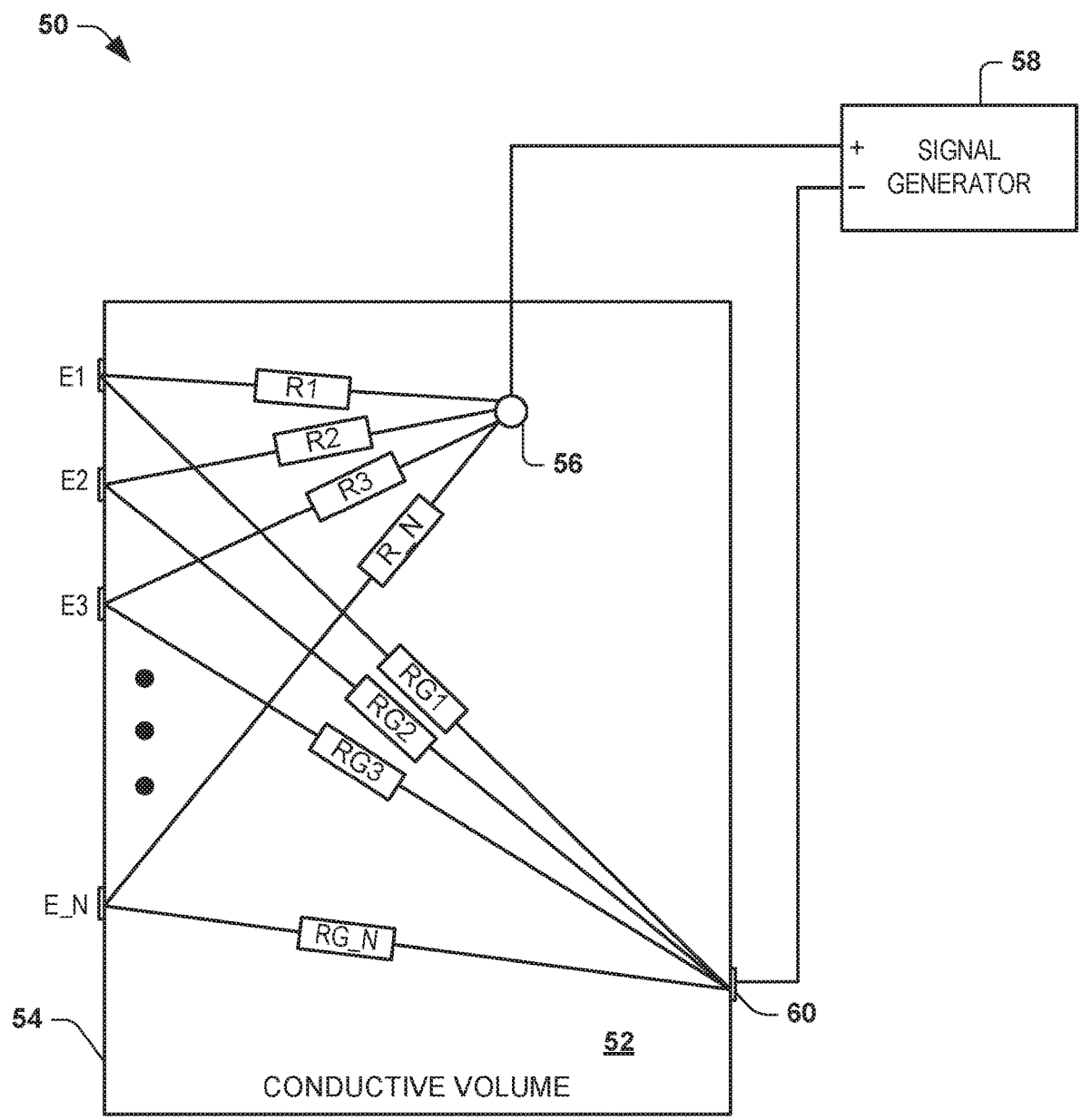
FIG. 2 depicts an example of a volume conductive media which is mostly resistive, and electrical stimulation being injected by a unipolar lead.

As a further example, FIG. 2 depicts a configuration of a localization system 50 that includes a volume of conductive media 52, which is mostly resistive (e.g., corresponding to conductive volume 14). As demonstrated, a plurality of sensor electrodes E1, E2, E3 through E_N (where N is a positive integer denoting the number of sensor electrodes. The sensor electrodes E1, E2, E3 through E_N can be distributed substantially evenly across an external surface of the conductive volume 52. The number N of electrodes is at least three and can be greater than 20 and, in some examples, can be equal to or greater than 200 electrodes. Examples of some arrangements of the sensor electrodes E1, E2, E3 through E_N that can be utilized are disclosed in the above-incorporated PCT/US2009/063803.

A source electrode 56, which defines a unipolar lead, is positioned within the volume 52 at a location that is to be determined. A signal generator 58 is connected to provide electrical energy to the source electrode 56. As illustrated in the example of FIG. 2, the signal generator is coupled to the source electrode 56 and a ground electrode 60 that is positioned at known location on the conductive volume. For example, a positive terminal of the signal generator is coupled to the source electrode and a negative terminal of the signal generator is coupled to the ground electrode 60. While in the schematic illustration of FIG. 2, the ground electrode and the sensor electrodes E1-E_N are demonstrated as located on opposing sides of the volume 52, the position of the electrodes E1-E_N will typically be distributed evenly around the volume 52 (e.g., around the patient's thorax for cardiac localization). The ground electrode 60 can be positioned on the surface 54 of the conductive volume 52 at a user-selected location, which may be predetermined or arbitrary. The ground electrode can be part of the same arrangement of sensors E1-E_N or it can be a separate electrode.

The signal generator 58 thus can inject electrical energy (e.g., current or voltage) at the source electrode 56 and ground electrode 60. The configuration is depicted in FIG. 2. The unipolar lead is inserted inside the conductive volume and connects to the positive output of an electrical stimulator. The sensor electrodes E1-E_N thus are deposed on the surface of the volume conductor 52 to measure sensed electrical activity in response to unipolar stimulation resulting from the injected electrical energy. The resistance between each surface electrode and the unipolar lead is represented by R1, R2, R3 through R_N. The resistance between each sensor electrode E1-E_N and the ground electrode 60 is represented by RG1, RG2, RG3 . . . RG_N. The resistance between the unipolar lead and the ground electrode 60 is represented by R_P.

Figure 3:
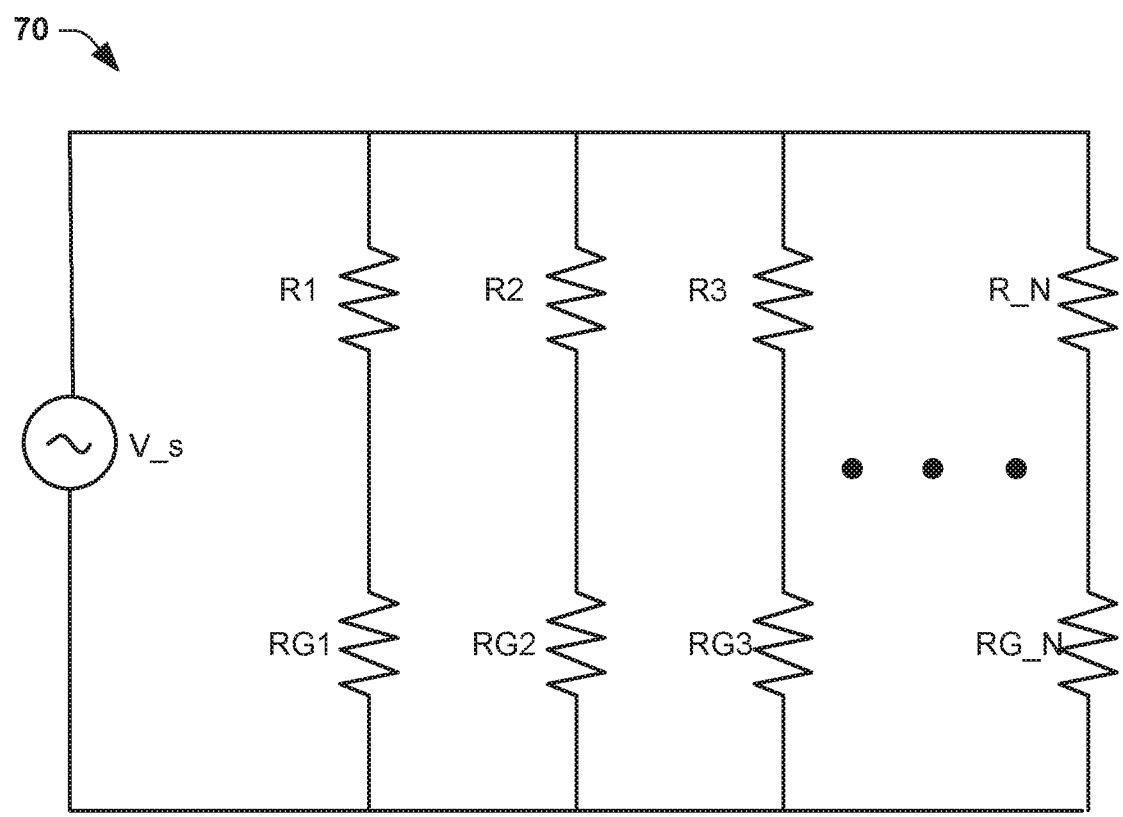
FIG. 3 depicts an example of a circuit approximating the flow of electrical current through the volume conductor of FIG. 2.

The electrical current that flows through the volume conductor 52 can be calculated by an approximation of the electrical configuration in the system 50, which approximation is demonstrated as the circuit 70 of FIG. 3. In the circuit 70 of FIG. 3, it can be assumed that conductivity ($\sigma$) and cross-section (A) of the current going through each recording electrode is substantially uniform in the conductive media. Thus, according to Pouillet's Law:

$R_i = L_i/(\sigma \cdot A)$ $R_{gi} = L_g/(\sigma \cdot A)$ where $L_i$ is the length (e.g., (e.g., spatial distance) between the electrode 56 and the a given one of the sensor electrodes E1-E_N, and $L_g$ is the length between the recording electrode and the ground electrode. The voltage measured from each of the sensor electrodes E1-E_N is indicated by $V_{m1}$, $V_{m2}$, $V_{m3}$ . . . $V_{m\_N}$. For each electrode i, the passing through current can be expressed as follows:

$I = V_0/(R_i + R_{gi})$ and the voltage measurement from this electrode is:

$V_{mi} = I \cdot R_{gi}$

Therefore, $$V_{mi} = \frac{V_0 \cdot R_{gi}}{R_i + R_{gi}}$$

Assuming $\sigma$ and A are constants, the relationship for each electrode i can be rewritten as follows:

$$V_0 = \frac{V_{mi}(L_i + L_{gi})}{L_{gi}} \quad (1)$$

As mentioned above, for a given electrode arrangement on the surface 54, the locations for each of the electrodes (including ground electrode 60) are known (e.g., stored in sensor location data 26). Thus, the location $r_i$ of each electrode i and the distance $L_{gi}$ between the ith electrode and a ground electrode are known or can be derived from geometry data 24. The location calculator 30 thus is configured to compute a location of the source electrode 56, represented as $r_0$.

Based on Eq. (1), each electrode measurement can be used to calculate the voltage of the source, and each source voltage, when accurately determined, leads to the same quantity. Thus, the difference between determined source voltages for a given pair of electrodes i and j, selected from the set of available N electrodes, should approach zero, which can be expressed as follows:

$$\frac{V_{mi}(L_i + L_{gi})}{L_{gi}} - \frac{V_{mj}(L_j + L_{gj})}{L_{gj}} \to 0, \forall i \neq j \quad (2)$$

From Eq. (2), a minimization function for computing a location for the source $r_0$ can be represented as follows:

$$E(r_0^*) = \min_{r_0 \in \mathbb{R}^3} \sum_{(i,j)} \left| \frac{V_{mi}(|r_i - r_0| + L_{gi})}{L_{gi}} - \frac{V_{mj}(|r_j - r_0| + L_{gj})}{L_{gj}} \right|^2 \quad (3)$$

where $r_i$ and $r_j$ define the locations of the ith and jth electrodes, respectively, and $r_0$ is the location of the source that is being determined.

Eqs. (2) and (3) are based on the assumption that $\sigma$ and A are constants, which may not be true in reality; however, for electrodes spatially residing proximal to each other (e.g., to define a neighborhood of nearby electrodes), the values of $\sigma$ and A should be close. Therefore, the electrodes can grouped into subsets, $S_k$, where k=1 . . . K (K denoting the number of subsets). Each subset of electrodes is considered to reside in a respective neighborhood where the assumption that $\sigma$ and A are constants is presumed to be true for each such neighborhood. Each subset $S_k$ can be a contiguous spatial region within the volume 52. Alternatively or additionally, the subsets of electrodes can be grouped into respective subsets based on a determined impedance between respective pairs of electrodes and/or associated homogeneity of various regions throughout the volume (e.g., determined by respective calculators 40 and 42). For instance, each subset $S_k$ can include pairs of electrodes determined to have an impedance and/or a homogeneity index within a common range that has been assigned to each group. Thus, the different subsets can vary depending on patient anatomy within the portion of the volume where the source is being localized. Based on such assumptions for each subset of electrodes, the following minimization can be expressed as follows:

$$E(r_0^*) = \min_{\substack{r_0 \in \mathbb{R}^3 \\ r_i, r_j \in S_k}} \sum_{k=1}^{K} \sum_{\substack{i \in S_k \\ j \in S_k}} \left| \frac{V_{mi}(|r_i - r_0| + L_{gi})}{L_{gi}} - \frac{V_{mj}(|r_j - r_0| + L_{gj})}{L_{gj}} \right|^2 \quad (4)$$

where $r_{ik}$ and $r_{jk}$ are the respective locations of ith and jth electrodes in group $S_k$, k=1 ... K, (K being a positive integer denoting the number of groups $S_k$) and $r_0$ is the location of the source.

In each of the minimization functions represented in Eqs. (3) and (4), it is understood that the voltage of source does not need to be calculated, such that there is no ill-posed inverse problem to solve. Instead, the localization calculator 30 computes the location based on the electrode measurements and the known electrode locations (e.g., in the absence of having to solve the inverse problem).

As lengths $L_{gi}$ and $L_{gj}$ are constants based on known locations $r_i$ of measurement electrodes and a fixed ground location, while $|r_i - r_0|$ is not a linear operator, the minimization problem cannot be solved as linear problem. Nonetheless, various numerical methods exist to solve the minimization problem presented herein, such as represented in Eqs. (3) and (4), and to calculate the position of the source based on the measured electrical signals by the sensors and the known sensor locations. The numerical optimization methods can include a brute-force search method or an iterative method (e.g., Newton's method, gradient descent methods, conjugate gradient method or the like.

As one example, a brute force method can involve systematically choosing input values from within an allowed set and computing the value of the function 34 (e.g., from Eqs. (3) and/or (4)) according to the method shown in the following table.

| | |
|---|---|
| 1. | Partition the spatial domain within the volume conductor into a grid of voxels. |
| 2. | For each grid voxel, assume that is the location of catheter to be detected. The cost function (e.g., as set forth in Eq. (3) and/or Eq. (4)) can be evaluated. |
| 3. | After evaluating cost function at all grid points, identify the grid point that provides the smallest cost function among all grid points. |
| 4. | To increase accuracy, if desired, resolution, another round of partitioning of the domain around the point identified in 3 can be performed. Then, the method can repeat 2-3. |
| 5. | The method can repeat 1-4 until a desired resolution is achieved. The desired resolution can be set in the beginning. The point location corresponding to the smallest cost function at the desired resolution grid can be stored in memory as the location data corresponding to the source location within the volume conductor. |

As mentioned above, other methods, such as Gauss-Newton's method or gradient descent methods, can be used to solve this minimization problem (e.g., from Eqs. (3) and (4)). Additionally, or alternatively, in each of the examples localization disclosed herein (e.g., the minimization functions presented in Eqs. (3) and (4)), the respective minimization function can be seeded with a priori information regarding approximate location in the given coordinate system facilitate the determination of the source location. For instance, the initial location can be based on a previously determined source location in the given coordinate system. Alternatively, a location within a region of interest can be used to seed the numerical method to facilitate the minimization function.

Figure 6:
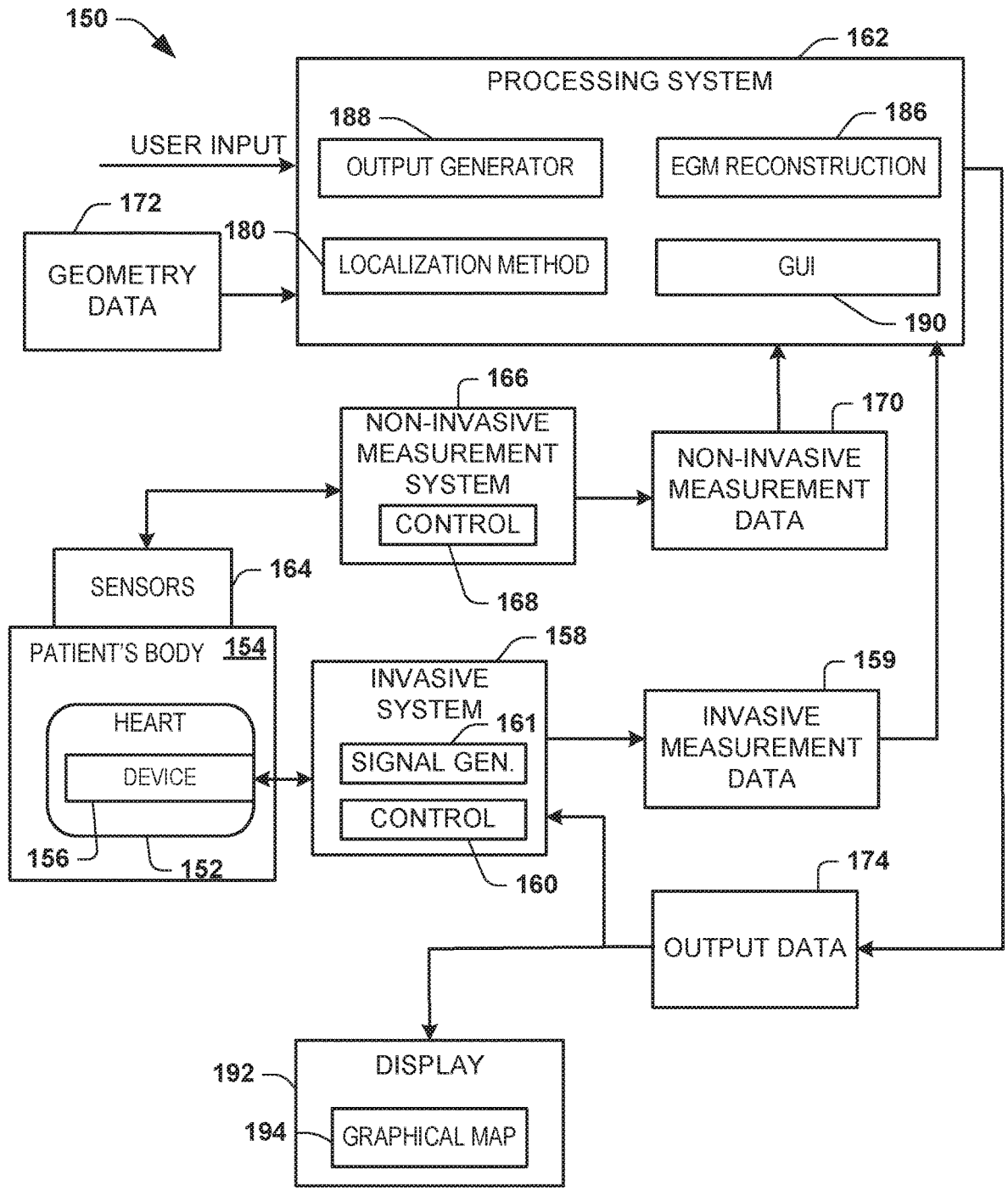
FIG. 6 depicts an example of a navigation and mapping system.

FIG. 6 depicts an example of another system 150 that can be utilized for localizing one or more sources of electrical signals within a volume of interest, such as a patient's body 154. The system 150 can be employed in conjunction with performing diagnostics and/or treatment of a patient. In some examples, the system 150 can be implemented to generate corresponding graphical outputs for signals and/or graphical maps for a patient's heart 152, including the position of a source, in real time as part of a procedure (e.g., monitoring of signals during an electrophysiology study). Additionally or alternatively, the system 150 can be utilized as part of a treatment procedure, such as to help guide a physician to navigate a delivery device to a desired target site or region (e.g., containing identified arrhythmogenic electrical activity).

For example, an invasive device 156, such as a catheter, can be inserted into a patient's body 154. The device 156 includes one or more electrodes (e.g., unipolar leads) coupled to an invasive system 158 configured to deliver electrical energy that can be localized. The device 156 can apply the energy as a localization-specific signal, a pacing signal or to deliver another therapy, such as to electrically affect tissue (e.g., providing electrical stimulation therapy, or controlling delivery of chemical therapy, sound wave therapy, thermal therapy or any combination thereof).

The invasive system 158 can include a control 160 configured to control the signal generator 161 to apply the localization signal at one or more electrodes of the device 156. For example, the control 160 can control parameters (e.g., current, voltage, repetition rate, trigger delay, sensing trigger amplitude) of the signal generator 161 for delivering therapy (e.g., ablation or stimulation) via the electrode(s) to one or more location of the heart 152. The control 160 can set the therapy parameters and apply stimulation based on automatic, manual (e.g., user input) or a combination of automatic and manual (e.g., semiautomatic) controls. The invasive system 158 can also be configured to measure electrical activity via electrodes on the device 156, process the measured signals and provide corresponding invasive measurement data 159.

Additionally, the localization signals generated by signal generator 161 and applied to electrodes on the device 156 can be measured by a plurality of sensors 164 attached to the body 154 at locations known in a three-dimensional coordinate system. The sensors 164 thus can sense electrical activity, including signals corresponding to the applied localization signals. The sensors 164 can also sense other electrical signals, such as corresponding to real-time electrograms for the patient's heart.

The placement of the device 156 can be guided via a localization method 180, which can operate to localize the device 156 employing a minimization function, such as disclosed herein. The localization method 180 can correspond to the location calculator 30, including the sensor selector 38 and calibration engine 36. For example, the localization method 180 thus can evaluate a cost function by minimizing the difference between source voltages determined for different pairs of the plurality of sensors. As disclosed herein, the sensor measurements used by the localization method have known locations defined by geometry data 172, and the sensors can be non-invasive and/or invasive. Thus, the source voltages for non-invasive sensors are determined based on non-invasive measurement data 170 and geometry data 172, and source voltages for invasive sensors are determined based on invasive measurement data 159 and geometry data 172. The guidance can be automated, semi-automated or be manually implemented based on information provided. During localization, the unipolar source electrode on the device 156 can contact or not contact the patient's heart 152, endocardially or epicardially.

As a further example, the invasive system 158 can be located external to the patient's body 154 and be configured to control therapy that is being delivered by the device 156. For instance, the system 158 can also control electrical signals provided via a conductive link electrically connected between the delivery device (e.g., one or more electrodes) 156 and the system 158. One or more sensors (not shown but could be part of the device) can also communicate sensor information back to the system 158.

The position of the device 156 in the heart 152 in three-dimensional space can be determined by performing localization as disclosed herein, which can be tracked intraoperatively via an output system 162 when implemented during a procedure. The location of the device 156 and the therapy parameters thus can be analyzed to help control therapy. Additionally, the application of therapy (e.g, manually in response to a user input or automatically provided) can cause a timestamp or other time identifier to be tagged (e.g., as metadata) to the measurement data to identify when the therapy is applied and trigger localization to identify the location where the therapy is applied via the device 156. Other metadata describing the therapy (e.g., type, delivery parameters etc.) can also be stored with the measurement data.

Before, during and/or after delivering a therapy (e.g., via the system 158), one or more of the non-invasive measurement system 166 or invasive system 158 can be utilized to acquire electrophysiology information for the patient. The measurement system 166 can acquire navigation signals and mapping signals simultaneously to facilitate concurrent mapping and navigation. In the example of FIG. 6, one or more sensors 164 can be implemented as an array or other configuration for recording patient electrical activity. As one example, the sensors 164 can correspond to a high-density arrangement of body surface sensors that are distributed over a portion of the patient's torso for measuring electrical activity associated with the patient's heart (e.g., as part of an electrocardiographic mapping procedure). An example of a non-invasive sensor array that can be used is shown and described in the above-incorporated International application No. PCT/US2009/063803, filed 10 Nov. 2009. Other arrangements and numbers of sensors 164 can be used. As an example, the sensors 164 can be a reduced set of sensors, which does not cover the patient's entire torso and is designed for measuring electrical activity for a particular purpose (e.g., an array of electrodes specially designed for analyzing AF and/or VF) and/or for monitoring a predetermined spatial region of the heart.

Sensors located on the device 156 can be utilized separately or in conjunction with the non-invasive sensors 164 for mapping electrical activity for an endocardial surface, such as the wall of a heart chamber, as well as for an epicardial surface. In each of such example approaches for acquiring real time patient electrical information, including invasively via the device 156, non-invasively via the sensors 164, or a combination of invasive and non-invasive sensing, the real time sensed electrical signals are provided to its corresponding measurement system 158, 166. Similar to the invasive system 158, the measurement system 166 can include appropriate controls and signal processing circuitry 168 for providing corresponding measurement data 170 that describes electrical activity detected by the sensors 164. The measurement data 170 can include analog and/or digital information (e.g., corresponding to electrogram data acquired by sensors 164). Thus, the measurement data 159 and 170 can correspond to the measured electrical signals used for localization, as disclosed herein.

The control 168 can also be configured to control the data acquisition process (e.g., sample rate, line filtering) for measuring electrical activity and providing the measurement data 170. In some examples, the control 168 can control acquisition of measurement data 170 separately from the invasive system operation, such as in response to a user input. In other examples, the measurement data 170 can be acquired concurrently with and in synchronization with specific signals applied by the signal generator 161 for purposes of localization. For instance, appropriate time stamps can be utilized for indexing the temporal relationship between the respective measurement data 159 and 170 and delivery of localization signals. The localization signals can be unique signals applied by the signal generator specifically to enable the localization. Additionally or alternatively, the signal generator can apply the localization signal, automatically or in response to a user input, for delivering a therapy. In either example, the non-invasive measurement system 166 can measure the body surface electrical activity via the sensor to provide corresponding measurement data 170. The processing system 162 thus can perform various signal processing and transformative methods, including a localization method 180 to localize each source according to the localization method disclosed herein.

The localization method 180 can be configured to implement any of the localization methods based on the measurement data 170 and/or 159 and associated geometry data 172. The coordinates determined by the localization method 180 can be utilized by an output generator 188 provide the output data 174. The output data 174 can represent or characterize the position of the device in three-dimensional space based on coordinates of the source electrode determined according to the approach herein. Additionally, the location (or a corresponding path) can be displayed at the spatial locations across a cardiac envelope (e.g., on an epicardial or endocardial surface of the heart 152). The output generator 188 can display the location separately. In other examples, the location can be combined with other output data, such as to display location information on graphical map of electrical activity of the heart 152.

Since, in some examples, the measurement system 166 can measure electrical activity of a predetermined region or the entire heart concurrently (e.g., where the sensors 164 are evenly distributed over the entire thorax of the patient's body 154 at predetermined locations defined in the geometry data 172), the measurements are spatially and temporally consistent. Consequently, the accuracy in the resulting output location provided in the output data 174 can be increased when compared to other localization techniques, such as to supply the user with a more accurate and global information to facilitate monitoring and application of therapy. Additionally or alternatively, the localization can be continuous process and/or be synchronized with respect to the application of therapy provided by the system 158.

By way of further example, the electrical measurement data is obtained non-invasively via body surface sensors 164, electrogram reconstruction 186 can be programmed to compute an inverse solution and provide corresponding reconstructed electrograms based on the measurement data 170 and the geometry data 172. The reconstructed electrograms thus can correspond to electrocardiographic activity across an envelope, and can include static (three-dimensional at a given instant in time) and/or be dynamic (e.g., four-dimensional map that varies over time). Examples of inverse algorithms that can be utilized in the system 150 include those disclosed in U.S. Pat. Nos. 7,983,743 and 6,772,004, which are incorporated herein by reference. The EGM reconstruction 186 thus can reconstruct the body surface electrical activity measured via the sensors 164 onto a multitude of locations on an envelope (e.g., greater than 1000 locations, such as about 2000 locations or more). In other examples, the output system 162 can compute electrical activity over a sub-region of the heart based on electrical activity measured invasively, such as via the device 156 (e.g., including a basket catheter or other form of measurement probe).

As disclosed herein, the reconstruction envelope (e.g., cardiac envelope) can correspond to a three-dimensional surface geometry corresponding to a patient's heart, which surface can be epicardial or endocardial. Alternatively or additionally, the envelope can correspond to a geometric surface that resides between the epicardial surface of a patient's heart and the surface of the patient's body where the sensors 164 have been positioned. Additionally, the geometry data 172 that is utilized by the electrogram reconstruction 186 can correspond to actual patient anatomical geometry, a preprogrammed generic model or a combination thereof (e.g., a model that is modified based on patient anatomy). The location computed via the localization method 180 can be co-registered with the geometry data 172 (e.g., anatomical geometry).

Similar to as described with respect to FIG. 1, the geometry data 172 may be in the form of graphical representation of the patient's torso, such as image data acquired for the patient. Such image processing (e.g., imaging processing 104) can include extraction and segmentation of anatomical features, including one or more organs and other structures, from a digital image set. Additionally, a location for each of the sensors 164 used for source localization, including non-invasive and/or invasive sensors, can be included in the geometry data 172, such as by acquiring the image while the electrodes are disposed on the patient and identifying the electrode locations in a coordinate system through appropriate extraction and segmentation.

As another example, a first set of non-invasive sensor electrodes can be secured around the thorax before imaging (e.g., via CT or MRI), and the locations of such electrodes can be determined via image processing. Some or all of the these sensors can then be used subsequently to locate another set of sensors fixed within the patient's body 154, such as endocardially, epicardially or other positions fixed within the body. Other non-imaging based techniques can also be utilized to obtain the position of the electrodes in the sensor array in the coordinate system, such as a using a digitizer, self-discovery or manual measurements, which can be stored in the geometry data 172. Once the locations of the sensors (invasive and/or non-invasive sensors) have a known location, their measurements can be selectively used by the localization method 180, as disclosed herein.

The geometry data 172 can correspond to a mathematical model, such as can be a generic model or a model that has been constructed based on image data for the patient. Appropriate anatomical or other landmarks, including locations for the sensors 164 can be identified in the geometry data 172 for display in conjunction with computed location information for the device. The identification of such landmarks and can be done manually (e.g., by a person via image editing software) or automatically (e.g., via image processing techniques).

By way of further example, the geometry data 172 can be acquired using nearly any imaging modality based on which a corresponding representation of the geometrical surface can be constructed, such as described herein. Such imaging may be performed concurrently with recording the electrical activity that is utilized to generate the patient measurement data 170 or the imaging can be performed separately (e.g., before or after the measurement data has been acquired).

The output generator 188 can generate corresponding output data 174 that can in turn be provide a corresponding graphical output in a display 192, such as including an indication of location for the device 156. The location can be displayed on graphical model of patient anatomy or superimposed on the electrocardiographic map 194. The location can take other forms to provide guidance to the user, such as disclosed herein.

A graphical user interface (GUI) 190 can be employed to interact with the processing system 162 and/or the systems 158 and/or 166. For example, the GUI can be used to set parameters associated with the displayed graphical representation, corresponding to an output visualization of the computed map, such as including selecting a time interval, a type of information that is to be presented in the visualization and the like can be selected in response to a user input. Additionally, a user can employ the GUI 190 to selectively program one or more parameters (e.g., models and spatial thresholds, filter parameters and the like) and/or configure the minimization function utilized by the localization method 182 (e.g., setting a desired resolution, associating sensor pairs, defining groups of sensors and the like).

Additionally, in some examples, the output data 174 can be utilized by the invasive system 158 in connection with controlling delivery of therapy or monitoring electrical characteristics. The control 160 that is implemented can be fully automated control, semi-automated control (partially automated and responsive to a user input) or manual control based on the output data 174. In some examples, the control 160 of the invasive system 158 can utilize the output data 174 to control one or more therapy parameters. As an example, the control 160 can control delivery of pacing therapy to a site of the heart (e.g., epicardial or endocardial wall) based on one or more arrhythmia drivers identified. In other examples, an individual can view the map 194 generated in the display to manually control the therapy system at a location determined based on this disclosure. Other types of therapy and devices can also be controlled based on the output data 174 and corresponding graphical map 194.

Figure 7:
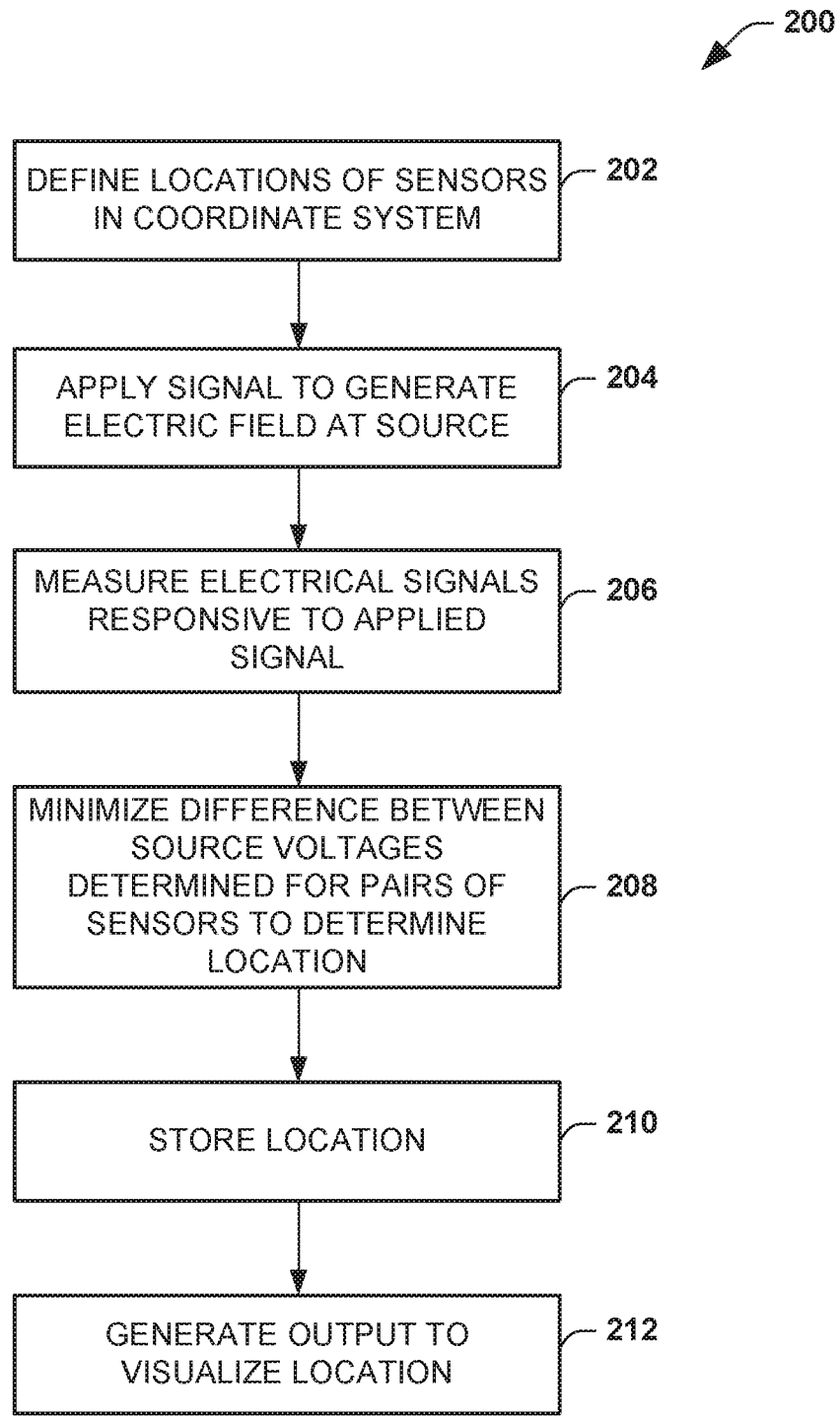
FIG. 7 is a flow diagram depicting a method of localization of a source within a conductive volume.

In view of the structural and functional features described above, certain methods will be better appreciated with reference to FIG. 7. FIG. 7 depicts an example of a method 200 for localizing a source object within the conductive volume. It is to be understood and appreciated that the illustrated actions, in other embodiments, may occur in different orders or concurrently with other actions. Moreover, not all features illustrated in FIG. 7 may be required to implement a method. It is to be further understood that the following method can be implemented in hardware (e.g., one or more processors, such as in a computer or an application specific integrated circuit), software (e.g., stored in a computer readable medium or as executable instructions running on one or more processors), or as a combination of hardware and software.

The method 200 can be implemented according to any of the systems or methods disclosed herein. The method 200 begins at 202 in which locations of sensors are defined for a given coordinate system (e.g., via geometry data 24 or 172). The locations of the sensors can be invasive and/or non-invasive, as disclosed herein. At 204, a signal is applied (e.g., by signal generator 16 or 161) to generate an electrical field at a source. At 206, electrical signals are measured (e.g., by sensors 18 or 164 and associated measurement system 20 or 166) in response to applied signal.

At 208, the difference between the source voltages determined for pairs of sensors are minimized (e.g., by solving minimization function 34) to ascertain a corresponding location of a source in a coordinate system. The minimization at 208 can be implemented collectively with respect to all of the sensors, assuming that sufficient homogeneous exist in the conductive volume. Alternatively, the minimization at 208 can be implemented with respect to a plurality of different subsets of electrodes and the location can be determined by aggregating the respective positions that have been determined for each of the respective subsets of sensors. The minimization can be implemented according to Eqs. (3) and/or (4) disclosed herein, for example.

At 210, the determined location is stored in memory. The memory can include any local or remote memory (e.g., volatile and/or non-volatile memory) that is accessible for retrieval, such as for use by a same or different computer from that implementing the method 200. The source location that is stored can thus represent spatial coordinates for the localized source. As mentioned, in some examples, there are multiple sources, which may be on the same or different probe, and each of such respective locations can be stored at 210 for each such source. At 212, the location for the object can be visualized such as in an output that is generated and provided to a display device. For example, the identified location can be overlaid in a graphical map of a patient's anatomy, such as a heart or other anatomic region where the source was localized to reside via the method 200. By determining the location and graphical map in a common coordinate system or (via registration or transform) visualization of the source electrode location, as well as a device carrying the field source for which the location was determined at 16, is facilitated.

In view of the foregoing structural and functional description, those skilled in the art will appreciate that portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. A system comprising:
a plurality of sensors configured to sense electrical activity at locations distributed across a conductive volume, locations of each of the plurality of sensors being predetermined with respect to a spatial coordinate system and stored in memory as geometry data;
a source electrode positioned within the conductive volume at an unknown location that is to be determined;
a signal generator to supply electrical energy to the source electrode, the electrical energy corresponding to a generated source voltage, which generates an electric field, there being a circuit path extending from the source electrode to an electrical ground at a position on an outer surface of the conductive volume, the electrical ground being coupled to the signal generator; and
a location calculator implemented as instructions executable by a computer processor in the system, the location calculator configured to compute the location of the source electrode by minimizing a difference between respective pairs of determined source voltages for a plurality of possible locations of the source electrode, wherein the determined source voltages are determined for the plurality of sensors, and each of the determined source voltages is determined for a respective one of the plurality of sensors based on a respective sensor measurement of voltage in response to the electric field and based on relative locations of the sensors determined from the geometry data.

2. The system of claim 1, wherein the location calculator is configured to compute the location of the source electrode based on the sensor measurements acquired concurrently for each of the plurality of sensors in response to the electric field.

3. The system of claim 2, wherein the plurality of sensors includes at least three electrodes distributed across the conductive volume.

4. The system of claim 1, wherein the geometry data specifying the predetermined location of each of the plurality of sensors comprises information generated by at least one of:
   self-discovery, wherein the spatial distribution of the sensors with respect to each other or a neutral point is computed based on a programmed sequence of current or voltage applied among the sensors,
   based on imaging data, or
   a digitizer.

5. The system of claim 1, further comprising a channel integrity detector implemented as instructions executable by a computer processor in the system, the channel integrity detector configured to identify one or more channels for exclusion from subsequent analysis based on one or more of correlation of a channel's signal with respect to signals of spatially neighboring channels, amplitude of the channel's signal, the channel being a short circuit or an open circuit, the geometry data and the sensor measurements for each channel identified for exclusion being made unavailable for the computation by the location calculator.

6. The system of claim 1, further comprising volume impedance data stored in the memory to characterize impedance of the conductive volume, the location calculator configured to account for variations in the impedance of the conductive volume based on the volume impedance data.

7. The system of claim 6, further comprising an impedance calculator implemented as instructions executable by a computer processor in the system, the impedance calculator configured to generate the volume impedance data based on electric fields sensed by the plurality of sensors in response to the electric field applied to the conductive volume.

8. The system of claim 1, further comprising a calibration engine implemented as instructions executable by a computer processor in the system, the calibration engine configured to group the plurality of sensors into multiple subsets of the plurality of sensors by assigning each sensor to one of the subsets, the location calculator configured to compute the location of the source electrode by minimizing the difference between source voltages determined for respective sensor pairs in at least one of the subsets of the plurality of sensors.

9. The system of claim 8, wherein the location calculator is configured to compute the location of the source electrode by aggregating source location values separately computed from corresponding sensor measurements acquired from at least two of the subsets of the plurality of sensors.

10. The system of claim 8, wherein the calibration engine is configured to automatically determine the assignment of the plurality of sensors to the multiple subsets of the plurality of sensors based on at least one of the volume impedance data, the geometry data or imaging data.

11. The system of claim 8, wherein the calibration engine is configured to determine the assignment of the plurality of sensors to the multiple subsets of the plurality of sensors in response to a user input selecting which sensors to include in each of the respective subsets of the plurality of sensors.

12. The system of claim 1, wherein the location calculator further comprises a sensor selector implemented as instructions executable by a computer processor in the system, the sensor selector configured to select at least three different pairs of sensors from the plurality of sensors, the location calculator configured to compute the position based on the sensor measurements from the selected pairs of sensors.

13. The system of claim 12, further comprising a channel integrity detector to identify for exclusion from subsequent analysis channels based on one or more of correlation of a channel's signal with respect to signals of spatially neighboring channels, amplitude of the channel's signal, the channel being a short circuit or an open circuit, to provide a remaining available subset of the plurality of sensors from which the sensor selector selects each of the selected pairs of sensors.

14. The system of claim 12, wherein the location calculator further comprises a homogeneity calculator implemented as instructions executable by a computer processor in the system, the homogeneity calculator configured to determine an indication of homogeneity of the conductive volume between respective pairs of sensors, the sensor selector selecting each of the selected pairs of sensors into a respective subset of sensors based on the indication of homogeneity.

15. The system of claim 14, further comprising an impedance calculator implemented as instructions executable by a computer processor in the system, the impedance calculator configured to determine impedance data representing impedance through the conductive volume, the homogeneity calculator determining the indication of homogeneity of the conductive volume based on the impedance data.

16. A method comprising:
   applying a localization signal to a source electrode positioned within a conductive volume and a ground electrode at a known location with respect to the conductive volume, the known location of the ground electrode being stored in memory as part of geometry data;
   sensing electrical activity at a plurality of sensor electrodes distributed across the conductive volume, a location of each of the plurality of sensor electrodes being predetermined with respect to a spatial coordinate system and stored in the memory as part of the geometry data, the electrical activity sensed at each of the plurality of sensor electrodes in response to the applied localization signal being stored in the memory as electrical measurement data; and
   computing the location of the source electrode by minimizing a difference between respective pairs of determined source voltages for a plurality of possible locations of the source electrode, wherein the determined source voltages are determined for the plurality of sensor electrodes, and the determined source voltage for each of the respective sensor electrodes is based on the localization signal applied to the source electrode as provided in the electrical measurement data and also based on relative locations of the sensor electrodes determined from the geometry data.

17. The method of claim 16, wherein computing the location of the source electrode further comprises:
   computing the source voltage associated based on the electrical activity sensed at each of the plurality of sensor electrodes and as a function of the location of the respective sensor electrode and the location of the ground electrode;
   selecting each of the pairs of the sensor electrodes; and
   computing the difference between the computed source voltage for each of the selected pairs of the sensor electrodes.

18. The method of claim 16, wherein prior to computing the location of the source electrode, the method further comprises:

grouping the plurality of sensor electrodes into a plurality of subsets of the sensor electrodes by assigning each sensor electrode to one of the plurality of subsets;

computing the location of the source electrode being separately for respective sensor pairs in at least two of the plurality of subsets of the sensor electrodes; and combining the location of the source electrode computed for each of the plurality of subsets of the sensor electrodes.

19. The method of claim 18, further comprising, prior to computing the location of the source electrode, calibrating a minimization function that is used in the computing, the calibration being implemented based on at least one of the geometry data, the electrical measurement data, channel detection data or in response to a user input.

20. One or more non-transitory computer-readable media storing data and instructions executable by a processor, wherein the data comprises:

geometry data representing locations of each of a plurality of sensors at locations distributed across an outer surface of a conductive volume; and measurement data representing sensed electrical measurements for each of the plurality of sensors, the sensed electrical measurements corresponding to an electric field generated in response to applying electrical energy to a source electrode located within the conductive volume, and wherein the instructions comprise a location calculator to compute a location of the source electrode within the conductive volume by minimizing a difference between respective pairs of determined source voltages for each of a plurality of possible locations of the source electrode, the determined source voltages are determined for multiple pairs of the plurality of sensors, and each of the determined source voltages is determined for each of the respective plurality of sensors based on the measurement data including the sensed electrical measurements as well as relative locations of the plurality of sensors determined from the geometry data.

* * * * *